United States Patent [19]

Fitzgerald

[11] Patent Number: 5,882,686
[45] Date of Patent: Mar. 16, 1999

[54] METHODS FOR THE PREVENTION AND TREATMENT OF UROGENITAL DISORDERS

[75] Inventor: Jamesina Anne Fitzgerald, Mason, Ohio

[73] Assignee: The Procter & Gamble Company, Cincinnati, Ohio

[21] Appl. No.: 923,831

[22] Filed: Sep. 4, 1997

Related U.S. Application Data

[63] Continuation of Ser. No. 568,852, Dec. 7, 1995, abandoned.

[51] Int. Cl.$^6$ ............................ A61K 33/24; A61K 31/33
[52] U.S. Cl. .......................... 424/653; 514/184; 514/931; 514/967
[58] Field of Search .............................................. 424/653

[56] References Cited

U.S. PATENT DOCUMENTS

| | | | |
|---|---|---|---|
| 4,049,817 | 9/1977 | Laber et al. | 424/270 |
| 4,514,421 | 4/1985 | Herschler | 418/110 |
| 5,221,664 | 6/1993 | Berkowitz et al. | 514/6 |
| 5,256,684 | 10/1993 | Marshall | 514/398 |

FOREIGN PATENT DOCUMENTS

| | | | |
|---|---|---|---|
| 962163 | 6/1950 | France. | |
| 0000994 | 12/1982 | France. | |
| 63-174926 | 7/1988 | Japan | A61K 31/29 |
| WO 92/01457 | 2/1992 | WIPO | A61K 33/24 |
| WO 95/32720 | 12/1995 | WIPO | A61K 33/24 |

OTHER PUBLICATIONS

Than, U Pe, et al., "The Alkaloids of Holarrhena Antidysenterica", Union of Burma Journal of Science and Technology, vol. 2, Dec. 1969, pp. 423–436.
Willard, F. L., et al., "Survey of Chemical Compounds Tested In Vitro Against Rumen Protozoa for Possible Control of Bloat", vol. 15, No. 5, Sep. 1967, pp. 1014–1019.
DuPont, H., et al., Symptomatic Treatment of Diarrhea With Bismuth Subsalicylate Among Students Attending a Mexican University, Gastroenterology, vol. 73, (1977), pp. 715–718.
DuPont, H., "Enteropathogenic Organisms: New Etiologic Agents and Concepts of Disease", Medical Clinics of North America, vol. 62, No. 5 (1978), pp. 945–960.
Wolfe, M., "The Treatment of Intestinal Protozoan Infections", Medical Clinics of North America, vol. 56, No. 3 (1982), pp. 707–720.
Journal of the American Medical Association, "Traveler's Diarrhea", vol. 253, No. 18 (1985), pp. 2700–2704.
DuPont, L., "Nonfluid Therapy and Selected Chemoprophylaxis of Acute Diarrhea", The American Journal of Medicine, vol. 78, Suppl. 6B (1985), pp. 81–90.
Johnson, P., et al., "Comparison of Loperamide With Bismuth Subsalicylate for the Treatment of Acute Traveler's Diarrhea", The Journal Of the American Medical Association, vol. 255, No. 6 (1986), pp. 757–760.
Steffen, R., "Anerkannte Prinzipien zur Prophylaxe und Therapie der Reisediarrhoe", Schweiz. med. Wschr. 116, Nr. 20 (1986), pp. 670–673 (translation provided).

DuPont, H., et al., "Prevention of Travelers' Diarrhea By the Tablet Formulation of Bismuth Subsalicylate", The Journal of the American Medical Association, vol. 257, No. 10 (1987), pp. 1347–1350.
White, N., "Drug Treatment and Prevention of Malaria", European Journal of Clinical Pharmacology, vol. 34 (1988), pp. 1–14.
D'Alessandro, A., "Amebiasis Then", American Journal of Tropical Medicine and Hygiene, vol. 41, No. 3, Suppl. (1989), pp. 38–39.
Steffen, R., "Worldwide Efficacy of Bismuth Subsalicylate in the Treatment of Travelers' Diarrhea", Reviews of Infectious Diseases, vol. 12, Suppl. 1 (1990), pp. S80–S86.
Long, E., et al., "Alga Associated with Diarrhea in Patients with Acquired Immunodeficiency Syndrome and in Travelers", Journal of Clinical Microbiology, vol. 28, No. 6 (1990), pp. 1101–1104.
Wolfe, M., "Acute Diarrhea Associated With Travel", The American Journal of Medicine, vol. 88, Suppl. 6A (1990), pp. 34S–37S.
Qadri, S.M.H., "Infectious Diarrhea: Managing a Misery that is Still Worldwide", Postgraduate Medicine, vol. 88, No. 5 (1990), pp. 169–184).
Farthing, M.J.G., et al., "Treatment and Prevention of Travellers' Diarrhoea", Gastroenterology International, vol. 5, No. 3 (1992), pp. 162–175.
Zinsser Microbiology, 20th ed., Appleton & Lange (1992), pp. 1161–1173.
Arduino, R., et al., "Travellers' Diarrhoea", Bailliere's Clinical Gastroenterology, vol. 7, No. 2 (1993), pp. 365–385.
Chak, A., et al., "Traveler's Diarrhea", Gastroenterology Clinics of North America, vol. 22, No. 3 (1993), pp. 549–561.
American Health Consultants, "Cryptosporidiosis in Milwaukee", vol. 12, No. 15 (1993), pp. 113–115.
Wittner, M., et al., "Parasitic Infections in AIDS Patients: Cryptosporidiosis, Isosporiasis, Microsporidiosis, Cyclosporiasis", Infectious Disease Clinics of North America, vol. 7, No. 3 (1993), pp. 569–586.
Weber, R., et al., "Disseminated Microsporidiosis Due to *Encephalitozoon Hellem*: Pulmonary Colonization, Microhematuria, and Mild Conjunctivitis in a Patient with AIDS", Clinical Infectious Diseases, vol. 17 (1993), pp. 415–419.
Kuhls, T., "Protozoal Infections of the Intestinal Tract in Children", Advances in Pediatric Diseases, vol. 8 (1993), pp. 177–202.

(List continued on next page.)

Primary Examiner—Russell Travers
Attorney, Agent, or Firm—Kirsten K. Stone; Mary Catherine Hentz; Douglas C. Mohl

[57] ABSTRACT

The subject invention encompasses methods for the prevention and treatment of a human or lower animal subject having a urogenital disorder caused or mediated by one or more parasitic protozoa comprising administering bismuth to the subject.

8 Claims, No Drawings

OTHER PUBLICATIONS

Scott, D., et al., "Treatment of Gastrointestinal Infections", Bailliere's Clinical Gastroenterology, vol. 7, No. 2 (1993), pp. 477–499.

Martindale, The Extra Pharmacopoeia, "Gastro–Intestinal Agents", Thirtieth Ed., The Pharmaceutical Press (1993), p. 872.

Health, "Are Milwaukee–Type Parasites Floating in My Drinking Water?" (1993), p. 14.

Sun, T., et al., "Intestinal Microsporidiosis: Report of Five Cases", Annals of Clinical and Laboratory Science, vol. 24, No. 6 (1994), pp. 521–532.

American Drug Index, 38th Ed. (1994), pp. 568–569.

Upcroft, P., "Multiple Drug Resistance in the Pathogenic Protozoa", Acta Tropica, vol. 56 (1994), pp. 195–212.

Herwaldt, B., et al., "Infections with Intestinal Parasites in Peace Corps Volunteers in Guatemala", Journal of Clinical Microbiology (1994), pp. 1376–1378.

Physicians' Desk Reference, 48th Ed. (1994), pp. 724–726.

Jernigan, et al., "Parasitic Infections of the Small Intestine", Gut, vol. 35, No. 3 (1994), pp. 289–293.

Fritsche, T., et al., "Introduction to Diagnostic Parasitology: Biologic, Clinical, and Laboratory Considerations", Manual of Clinical Microbiology, Sixth Ed., ASM Press (1995), pp. 1141–1144.

Chevalier, C., et al., "Bilan Des Antiparasitaires A Usage Veterinaire: Antihelminthiques, Anticoccidiens, Antifongiques, Ectoparasiticides" (translation attached), Laboratory of Therapeutic Chemistry, College of Pharmacy, 37042 Tours Cedex, pp. 624–630.

Cavier, R., "Erude des propriérés parasiticides de quelques complexes bismuthiques de l'oxy–8 quinoléine", Annales pharmaceutiques francaises, 1973, 31, No. 4, pp. 173–178 (translation attached).

Pitlik, S., et al., "Cryptosporidial Cholecystitis", The New England Journal of Medicine, vol. 308, No. 16 (Apr. 21, 1983), p. 967.

Berque et al, 123CA:350367j, 1995.

Berque, Jean 123CA:350367j, Oct. 19, 1995.

Wittna et al, Parasitic Diseases, vol 7(3) 569–586, 1993.

Cavier et al, 1973, Annales Pharmaceutiques Francaises vol. 31(4) pp. 273–278 (Abstract).

METHODS FOR THE PREVENTION AND TREATMENT OF UROGENITAL DISORDERS

This is a continuation of application Ser. No. 08/568,852, filed on Dec. 7, 1995.

BACKGROUND OF THE INVENTION

While many industrialized countries have come to regard parasitic infection as a problem of impoverished developing countries, this is far from the truth. The incidence of parasitic infection, especially of the urogenital tract, continues to present a serious health concern. For example, in the United States in some areas, the incidence of urogenital infection due to *Trichomonas vaginalis* is reported to be as high as fifty percent with twenty to fifty percent of infected women and ninety percent of infected men being asymptomatic. *Zinsser Microbiology*, 20th Edition, 1173 (1992). Additionally, in the case of urogenital infection, incidence of infection is notoriously underestimated due to physicians prescribing broad spectrum antibiotics rather than isolating the offending, fastidious pathogen and the failure of physicians to report sexually transmitted vaginal diseases. Traditional treatment regimens for such infections consist of administration of a selective action antibiotic. However, antimicrobial resistance to such drugs raises concern about the ability to effectively treat parasitic infections in the future. Therefore, the need for effective anti-parasitic treatment therapies continues to grow.

It has been discovered by the present invention that the administration of bismuth salts may be effective for the prevention and/or treatment of urogenital disorders caused or mediated by parasitic protozoa. Thus, an object of the present invention is to provide a safe and effective method of preventing and/or treating urogenital disorders caused or mediated by parasitic protozoa. A further object of the invention is to provide such a method comprising the administration of bismuth.

These and other objects of the present invention will become readily apparent from the detailed description which follows.

SUMMARY OF THE INVENTION

The present invention relates to a method for treatment of a human or lower animal subject having a urogenital disorder caused or mediated by one or more parasitic protozoa comprising administering to the subject from about 50 milligrams to about 10,000 milligrams of bismuth, per day, for from about 1 to 56 days.

The present invention also relates to a method for prevention in a human or lower animal of a urogenital disorder caused or mediated by one or more parasitic protozoa comprising administering to the subject from about 50 milligrams to about 10,000 milligrams of bismuth, per day, for from about 1 to 28 days.

DETAILED DESCRIPTION OF THE INVENTION

The methods of the present invention comprise the prevention and/or treatment of urogenital disorder caused or mediated by one or more parasitic protozoa. Such urogenital disorders are prevented and/or treated by the administration of bismuth. The components of the present invention are more fully defined below.

Urogenital Disorder

The term "urogenital disorder", as used herein, encompasses any infection, disease or other disorder of the urinary and/or reproductive systems, caused or mediated by one or more parasitic protozoa. Such disorders include one or more of the following conditions: vaginitis; vaginal burning, itching, discharge; dysuria; ulcerative lesions; painful urination; prostatitis; urethritis; epidiymitis; urethral stricture; and any other urogenital condition commonly associated with infection by parasitic protozoa.

In immunocompromised subjects, urogenital disorders caused or mediated by parasitic protozoa may be more severe and life threatening than the common disorders listed above. Therefore, the term "urogenital disorder" also includes any condition commonly associated with protozoa infection in immunocompromised subjects including but not limited to foul smelling discharge, bleeding or purulent urogenital lesions, severe pruritus, painful dysuria, and microhematuria.

Parasitic Protozoa

Protozoa are unicellular, eucaryotic organisms which contain a nucleus, or nuclei, and cytoplasm. The term "parasitic protozoa", as used herein, refers to Protozoa such as *Trichomonas vaginalis*, and the microsporidia of the genera Pleistophora, Nosema, and Encephalitozoon. Preferred parasitic protozoa are *Trichomonas vaginalis, Encephalitozoon hellem*, and combinations thereof. Most preferred parasitic protozoa is *Trichomonas vaginalis*. These organisms are fully described in *Manual of Clinical Microbiology*, Sixth Edition, 1204–1205, 1213–1217, and 1225–1228 (1995), which is incorporated herein by reference.

Diagnosis of urogenital disorders caused or mediated by parasitic protozoa may be accomplished by any method commonly used in the medical community. Such methods are fully described in *Manual of Clinical Microbiology*, as referenced above.

Bismuth

The methods of treatment and/or prevention in the present invention involve administration of bismuth. As used herein, the quantity of bismuth is by weight of elemental bismuth.

The preferred duration of bismuth administration will vary according to the specific urogenital disorder to be treated and the physical condition of the subject being treated. In general, as a method of treatment, bismuth may be administered in an amount of from about 50 milligrams to about 10,000 milligrams, and preferably from about 50 milligrams to about 5000 milligrams, per day, for from about 1 to about 56 days, preferably for from about 2 to about 28 days, and most preferably for from about 7 to about 21 days.

In general, as a method of prevention, bismuth may be administered in an amount of from about 50 milligrams to about 10,000 milligrams, and preferably from about 50 milligrams to about 5000 milligrams, per day, for from about 1 to about 21 days, and preferably for from about 1 to about 14 days. In a method of prevention, bismuth may be administered prior to potential exposure to parasitic protozoa. Such administration of bismuth may vary depending on the likelihood of parasitic protozoa exposure and condition of the subject and may be commenced at any time deemed beneficial by the medical community including from about 1 to about 7 days, from about 2 to about 5 days, and from about 3 to about 4 days, prior to potential exposure.

In the present methods, the term "bismuth", as used herein, includes bismuth in the form of a pharmaceutically-acceptable salt, bismuth or bismuth salt in the form of an organic or other complex which contains bismuth as an active ingredient, and mixtures thereof. Such organic complexes include 2,2'-spirobi[1,3,2-benzodox-abismole]. Preferably, bismuth is administered in the present methods as a pharmaceutically-acceptable salt. Such bismuth salts include bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention.

The bismuth useful herein may be administered alone, or in combination with other pharmaceutically-acceptable components in a bismuth-containing composition. A variety of such compositions containing bismuth salts are commercially available. Such compositions include DeNol, containing tripotassium dicitrato bismuthate (by Brocades); Bislumina, containing bismuth aluminate (by Mazuelos); Roter, containing bismuth subnitrate (by Roterpharma); Devrom®, containing bismuth subgallate (by The Parthenon Co., Inc.); and Pepto-Bismol®, containing bismuth subsalicylate (by The Procter & Gamble Company).

As used herein, the term "administering" refers to any method which, in sound medical practice delivers the compounds or compositions used in this invention intravaginally to the subject to be treated in such a manner so as to be effective in the treatment of the urogenital disorder. Therefore, the bismuth may be administered in the form of a douche, douche powder, suppository, tablet, ointment, cream, gel, mousse, foam, or any other form which would administer bismuth intravaginally to the subject. The delivery systems are described in detail in *Remington's Pharmaceutical Sciences*, 18th Edition, 1609–1614, 1632, 1525, 1519–1544, 1597–1614, 1633–1675, (1990); and Ansel, et al., *Pharmaceutical Dosage Forms and Drug Delivery Systems*, Fifth Edition, 373–389, (1990).

The following non-limiting examples illustrate the methods and uses of the present invention.

EXAMPLE I

A young college coed visits a campus health center for her routine annual gynecological exam, complaining of vaginal irritation. Upon examination of the vagina, the physician observes the presence of a foamy, yellowish-green discharge and chafing of the vagina, vulva, and perineum. Using a vaginal speculum, exudate is collected from the vaginal canal and a wet mount preparation is made promptly and analyzed microscopically. The presence of organisms, 5–20 m in length with a jerky type motion confirms the presence of *Trichomonas vaginalis*. The patient is treated by a method of the present invention. A composition containing bismuth subsalicylate is administered in a liquid douche delivering approximately 2500 mg of bismuth per liter of douching solution, twice daily (a total of 5000 milligrams of bismuth daily) for twenty-one days. Thereafter, vaginal samples from the patient are analyzed again, finding no trace of parasitic infection. The subject remains asymptomatic, and another vaginal analysis performed 5 months later is normal.

In the above example, tripotassium dicitrato bismuthate, bismuth tartrate, bismuth citrate, and bismuth subnitrate are substituted, respectively, for bismuth subsalicylate, with substantially similar results.

EXAMPLE II

A male AIDS patient, who recently recovered from cryptosporidial diarrhea, reports genital irritation to his primary health care provider. Upon examination of the patient's penis, a small, purulent lesion is observed one centimeter from the urethral opening. A thin smear of the exudate is prepared and stained for 90 minutes with Modified Trichome-Blue Stain before oil immersion examination, while a midstream urine sample is collected, centrifuged, and examined promptly via light microscopy. The results show no indication of urinary infection; however, the presence of spores with coiled, polar tubules confirms an infection with *Encephalitozoon hellem*. The infection is treated by cleansing the lesion gently with non-medicated soap and topically applying a small amount of an ointment consisting of 10% bismuth subcitrate twice daily over the lesion for about 28 days, until the lesion has healed completely. Thereafter, visual inspection of the penis is performed finding slight scarring but no trace of parasitic infection.

EXAMPLE III

A young man, in the presence of his physician, confides to his future bride two days before their marriage that he is being treated for a urethral infection caused by *Trichomonas vaginalis*, reportedly from using a contaminated towel at his gym. The physician advises the groom to continue his current therapy until eradication of the parasite is complete. Clinical analyses indicate that the bride currently is not infected. Since the use of condoms was not considered due to religious beliefs, the bride is given 3500 milligrams of bismuth, administered as bismuth subnitrite in a vaginal suppository, for use thirty minutes before sexual intercourse. The suppositories are used for about 30 days, until her husband is determined to be free from infection. At this time, vaginal samples are taken from the wife and analyzed and no evidence of parasitic infection is found.

What is claimed is:

1. A method for treatment of a human or lower animal subject having a urogenital disorder caused or mediated by one or more parasitic protozoa comprising administering intravaginally to the subject from about 50 milligrams to about 10,000 milligrams of bismuth, in the form of one or more bismuth salts, per day, for from about 1 to 56 days.

2. The method of claim 1 wherein the bismuth is administered in the form of a douche at a level of from about 50 milligrams to about 5000 milligrams, per day.

3. The method of claim 1 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

4. The method of claim 1 wherein the parasitic protozoa are selected from the group consisting of *Trichomonas vaginalis*, *Encephalitozoon hellem*, and combinations thereof.

5. A method for the prevention in a human or lower animal subject of a urogenital disorder caused one or more parasitic protozoa comprising administering intravaginally to the subject from about 50 milligrams to about 10,000 milligrams of bismuth, in the form of one or more bismuth salts, per day, for from about 1 to 21 days.

6. The method of claim 5 wherein the bismuth is administered in the form of a vaginal suppository at a level of from about 50 milligrams to about 5000 milligrams, per day.

7. The method of claim 5 wherein the bismuth is selected from the group consisting of bismuth aluminate, bismuth subcarbonate, bismuth subcitrate, bismuth citrate, tripotassium dicitrato bismuthate, bismuth subgalate, bismuth subsalicylate, bismuth tartrate, and mixtures thereof.

8. The method of claim 5 wherein the parasitic protozoa are selected from the group consisting of *Trichomonas vaginalis*, *Encephalitozoon hellem* and combinations thereof.

* * * * *